United States Patent

Fraioli

[11] 3,961,301
[45] June 1, 1976

[54] HUMIDITY SENSOR
[75] Inventor: Anthony V. Fraioli, Essen Fells, N.J.
[73] Assignee: Plessey Incorporated, Melville, N.Y.
[22] Filed: Dec. 13, 1973
[21] Appl. No.: 426,953

[52] U.S. Cl. .............................. 338/35; 200/61.06
[51] Int. Cl.² .......................................... H01C 13/00
[58] Field of Search ..................... 338/13, 34, 35;
73/336.5; 200/61.06; 23/232 E, 254 E, 255 E; 340/235; 261/130; 219/543

[56] References Cited
UNITED STATES PATENTS

| | | | |
|---|---|---|---|
| 2,083,732 | 6/1937 | Moore et al. | 219/361 X |
| 2,543,384 | 2/1951 | Squier | 338/35 |
| 2,806,991 | 9/1957 | White | 338/34 X |
| 2,979,828 | 4/1961 | Westeren | 219/361 X |
| 3,345,496 | 10/1967 | DeLaney et al. | 338/35 |
| 3,478,191 | 11/1969 | Johnson et al. | 219/543 X |
| 3,479,257 | 11/1969 | Shaver | 23/254 E X |
| 3,496,336 | 2/1970 | Hingorany et al. | 219/543 X |
| 3,715,702 | 2/1973 | Nicholas | 338/35 |
| 3,868,492 | 2/1975 | Taylor | 219/203 |

Primary Examiner—C. L. Albritton
Attorney, Agent, or Firm—James J. Burke

[57] ABSTRACT

The operation of relative humidity sensors made from cobalt oxide on a non-conductive ceramic substrate is improved by (1) providing a porous, sputtered overcoat of polytetrafluoroethylene which renders the sensor surface non-wettable without affecting other properties, and (2) providing a printed heating element on the back surface of the sensor, enabling in situ degassing of chemisorbed or adsorbed impurities and regeneration of a nascent sensor surface.

5 Claims, 2 Drawing Figures

HUMIDITY SENSOR

BACKGROUND OF THE INVENTION

The present invention relates in general to relative humidity sensors and, more particularly, the invention relates to sensors made from cobalt oxide as the active element.

Procedures for manufacturing cobalt oxide humidity sensors or hygrometers are well known. The starting material is a cobalt oxide powder. As pure CoO powder is very expensive, the starting material is generally a mixture of CoO with some $Co_3O_4$, but the latter compound dissociates at about 900°C. so the completed sensor will be essentially CoO, the cobaltous oxide. This compound is stable up to its melting point, which is above 1800°C.

The finely divided powder, preferably minus 325 mesh, is mixed with an inert liquid vehicle and viscosifiers to form a screen-printable paste. A thin layer of the paste is then screen-printed in a desired pattern onto a dielectric, high-temperature resistant substrate, typically a high-alumina ceramic. The screened pattern is then dried and fired in air at a temperature in the range of 1350°C. to 1550°C. Electrodes can be performed on the substrate, co-fired with the paste, or applied in a subsequent operation. The latter is the more common approach, as it is generally desired to have the electrodes in a rather elaborate interdigitated pattern on the top surface. Conductive inks or pastes are used in the conventional manner.

Before such a sensor can be put to use, it must be accurately calibrated to determine the change in electrical resistance with relative humidity.

PRIOR ART

The production of cobalt oxide hygrometers is disclosed by Delaney et al in U.S. Pat. No. 3,345,596. The two patents of Nicholas, No. 3,703,697 and No. 3,715,702, disclose the use of humectants to increase water absorption on hygrometer surfaces of this same type. In one instance the oxide is converted in part to the oxychloride, and in the other, a coating of lithium chloride or polyethylene glycol is provided. Blythe et al, U.S. Pat. No. 3,105,214, disclose the use of a vapor-permeable ion-selective membrane on the sensor surface. This will swell up in a humid environment and transport water but not ions to the sensor surface. Charlson et al, U.S. Pat. No. 3,315,518, utilize granulated Teflon (TM) as a support for a hygroscopic liquid in a humidity sensor.

OBJECTS OF THE INVENTION

A general object of the present invention is to provide improved humidity sensors of the cobalt oxide type.

Another object of the present invention is to provide a cobalt oxide humidity sensor with a non-wetting surface.

A further object of the present invention is to provide a cobalt oxide humidity sensor that can be automatically cleaned and regenerated in operation.

Various other objects and advantages of the invention will become clear from the following description of embodiments thereof, and the novel features will be particularly pointed out in connection with the appended claims.

THE DRAWINGS

Reference will hereinafter be made to the accompanying drawings wherein.

DESCRIPTION OF EMBODIMENTS

Figure 1:
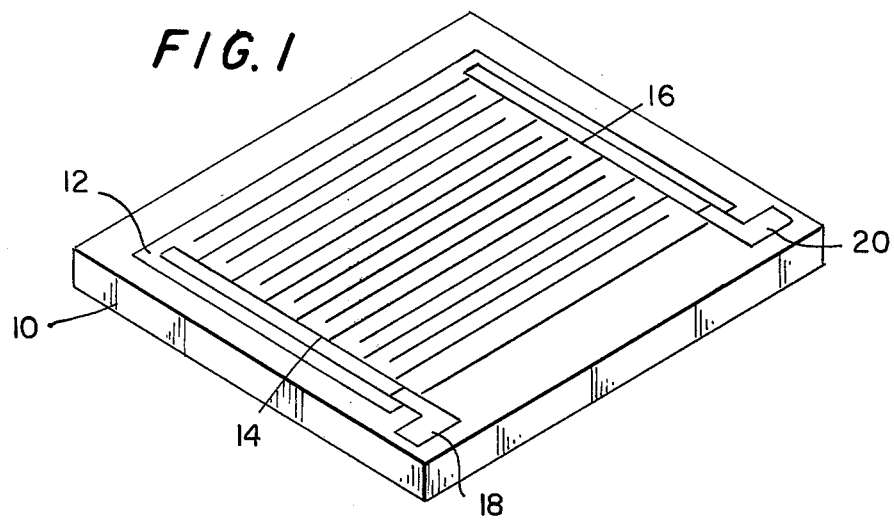
FIG. 1 is a perspective view of a typical humidity sensor.

A humidity sensor is illustrated in FIG. 1. The base is a ceramic substrate 10, typically a high alumina ceramic measuring about 0.5 by 0.5 by 0.040 inches. A fired-on layer 12 of cobalt oxide covers most of a major surface of substrate 10. Two interdigitated electrodes 14, 16 provide electrical contact to the sensor, and terminate in bonding pads 18, 20. The sensor is thus connectable to an RH measuring circuit.

One aspect of the present invention provides a porous, non-wetting surface for a cobalt-oxide humidity sensor. A problem which has heretofore limited the application of such devices has been susceptability of the sensor surface to corrosion or erosion in certain environments. Cobalt oxide is attacked by certain acids and salts, and of course any such attack will change its output characteristics. It would also be desirable to have a humidity sensor capable of measuring the equilibrium partial pressure of water vapor within a liquid environment, i.e. with the sensor immersed in a solution.

In the present invention these goals are achieved by providing a porous but non-wetting surface on the sensor. The material of choice is sputtered polytetrafluoroethylene (PTFE), commonly referred to as Teflon (TM).

The cobalt oxide humidity sensor may be prepared in accordance with the teachings of Delaney et al, referred to hereinabove, or in accordance with the refinements discussed hereinbelow. In either case, after the sensor is complete and the electrodes are attached, Teflon is sputtered onto the entire surface of the device, in a coating in the range of 0.01 to $10\mu$. The techniques of sputtering are believed to be well known to those skilled in the art. Briefly, satisfactory coatings are achieved in accordance with the present invention by argon sputtering. A sheet of Teflon is placed near the negative electrode and the sensor is in a plane with but not electrically connected to the positive electrode. The machine is pumped down to a high vacuum and about 0.02 mm of argon is bled into the system. A charge of about 20,000 volts is placed on the electrodes. The argon is ionized and the $Ar^+$ ions are accelerated toward the negative electrode but strike the Teflon, releasing molecules of the polymer, some of which strike the sensor.

The Teflon coating allows water vapor to reach the active cobalt oxide surface, but prevents ions from reaching it, by providing a contact angle of 0° at the interface. As is well known, the Teflon is inert and will neither absorb moisture or swell. Such a coating, when in contact with an aqueous phase, prevents the latter from either wetting or spreading, and vapor transport is thus the only mechanism for contact with the oxide surface. It is to be noted that the porosity of the film is such that capillary effects are avoided, i.e. surface tension holds the aqueous phase on the surface. Also, while Teflon is the preferred material in this service, it is believed that certain types of micro-porous polypropylene would also be effective (i.e. Celanese "Celguard").

Humidity sensors having a protective coating in accordance with the invention are operable in corrosive environments such as salt-spray chambers, and give an accurate relative humidity reading even when completely immersed.

Figure 2:
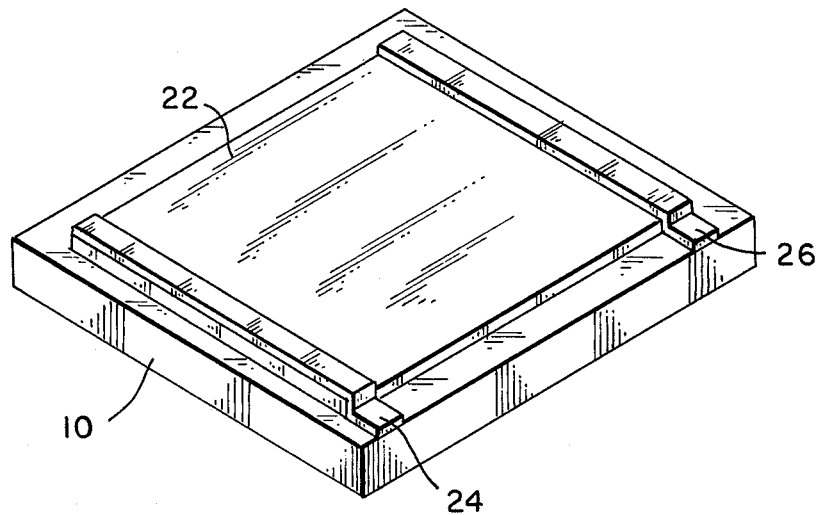
FIG. 2 is a perspective view of the rear side of a substrate, illustrating the printed heating element of the invention.

In the conventional manufacture of humidity sensors of this general type, it is not uncommon to subject the completed sensor to a "purification" heat treatment of about 400°C. to drive off any chemisorbed or adsorbed impurities which may have been occluded onto the surface of the device. Unfortunately, when a device is put into service it may be in such an environment that re-contamination is inevitable after a short period, requiring replacement of the sensor. For example, it is known that certain sensors used to monitor relative humidity of stack gases in an industrial plant had to be replaced on a weekly basis, a disagreeable and dangerous task. In a further aspect of the present invention this problem is eliminated by providing a thick-film heating element on the reverse side of the substrate. Such a pattern is illustrated in FIG. 2, which shows the reverse or back side of the substrate 10, upon which a heating element 22 terminating in bonding pads 24, 26 has been screened and fired. In manufacture of the sensor, it is generally possible to co-fire the sensor electrodes and the heating element simultaneously, if desired. Any suitable material may be employed, such as a Nichrome (TM) paste or ruthenium dioxide, and the geometry and thickness of the pattern calculated to provide heating to about 400°C. under given load conditions. This does not effect the cobalt oxide in any way, due to its inherent stability, but is sufficient to drive off all chemisorbed or adsorbed impurities and regenerate a clean, nascent surface.

As shown in FIG. 2, the heater element 22 is a pad covering substantially the entire surface of substrate 10, with conductives 24, 26 arrayed along two edges. This configuration is advantageous in that it minimizes thermal gradients in the substrate, and also minimizes the formation of hot-spots in film 22. This is because current will merely shunt around any local high resistance centers in the pad and not be forced through them, as could happen if element 22 were configured in a fine-lined serpentine array. A hot spot in the latter type of array could lead to a burnout condition.

With a heater on the reverse side of the sensor, the operator - without leaving the control room - can turn on the heater circuit for a nominal period (one hour is considered adequate) and regenerate the sensor automatically. Those skilled in the art will appreciate that when the heating element is employed, the ancillary equipment, housing, etc. must be of materials suitable for periodic temperature cycling.

It will be appreciated that both aspects of the present invention may be advantageously employed in certain applications. The surface coating protects the sensor from non-ionic contaminants such as sugars, etc. dissolved in an aqueous phase, and which might otherwise become irreversibly adsorbed on the sensor. The heater will drive off chemisorbed films by decomposition and remove any vapor contamination that might have reached the sensor surface. Obviously, the heater cannot be run at a temperature that would effect the Teflon or tend to decompose it, about 250°C.

Various changes in the details, steps, materials and arrangements of parts, which have been herein described and illustrated in order to explain the nature of the invention, may be made by those skilled in the art within the principle and scope of the invention as defined in the appended claims.

What is claimed is:

1. A humidity sensor comprising:
    a high-temperature resistant dielectric substrate;
    a fired layer of cobalt oxide on a major surface of said substrate;
    a pair of electrodes in contact with said cobalt oxide; and
    a porous, non-wettable coating covering at least said cobalt oxide layer.

2. The humidity sensor as claimed in claim 1, wherein said coating is sputtered polytetrafluoroethylene.

3. The humidity sensor as claimed in claim 1, wherein said substrate is a high-alumina ceramic.

4. The humidity sensor as claimed in claim 1, wherein said substrate has first and second major surfaces, said oxide layer, electrodes and coating are on said first major surface, and additionally comprising a fired, thick film heating element on said second major surface.

5. A humidity sensor comprising:
    a high-temperature resistant dielectric substrate;
    a fired layer of cobalt oxide on a major surface of said substrate;
    a porous, non-wetting coating of sputtered polytetrafluoroethylene over said fired layer;
    a pair of electrodes in contact with said cobalt oxide; and
    a fired, thick film heating element on the other major surface of said substrate.

* * * * *